United States Patent

Berger et al.

[11] 3,948,912
[45] Apr. 6, 1976

[54] NITROIMIDAZOLYL-TRIAZOLO-PYRIDAZINE COMPOUNDS AND THERAPEUTIC COMPOSITIONS

[75] Inventors: Herbert Berger, Mannheim-Kafertal; Rudi Gall, Grossachsen; Kurt Stach, Mannheim-Waldhof; Wolfgang Vomel; Rita Hoffmann, both of Mannheim, all of Germany

[73] Assignee: Boehringer Mannheim G.m.b.H., Mannheim-Waldhof, Germany

[22] Filed: Mar. 17, 1975

[21] Appl. No.: 559,285

[30] Foreign Application Priority Data
Apr. 17, 1974  Germany............................ 2418435

[52] U.S. Cl........... 260/250 AC; 424/200; 424/230; 424/250
[51] Int. Cl.².................................. C07D 237/26
[58] Field of Search ............................. 260/250 AC

[56] References Cited
UNITED STATES PATENTS
3,522,256  7/1970  Berger et al........................ 260/250

Primary Examiner—Richard J. Gallagher
Assistant Examiner—Anne Marie T. Tighe
Attorney, Agent, or Firm—Burgess, Dinklage & Sprung

[57] ABSTRACT

New nitroimidazolyl-triazolo-pyridazines of the formula:

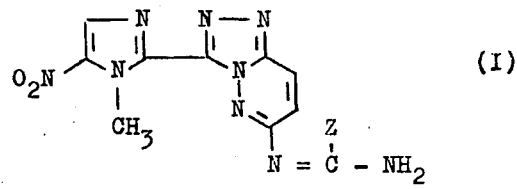

wherein
Z is methyl or amino which can be substituted by lower alkyl,
and the pharmacologically compatible acid-addition salts thereof, exhibit outstanding anti-microbial activity against bacteria and protozoa, and also systemic effectiveness.

6 Claims, No Drawings

NITROIMIDAZOLYL-TRIAZOLO-PYRIDAZINE COMPOUNDS AND THERAPEUTIC COMPOSITIONS

The present invention relates to new nitroimidazolyl-triazolo-pyridazine compounds and to therapeutic compositions and uses thereof.

A number of anti-microbially effective nitroimidazoles which are outstandingly effective against protozoa, for example Trichomonas, and against Salmonella have been disclosed; see, for example, German Pat. No. 1,920,635. A series of active nitroimidazolyl-triazolo-pyridazines containing amidine radicals is described in German Pat. No. 2,261,692. However, these known compounds lacked a broad spectrum of activity against both bacteria and protozoa and/or lacked satisfactory systemic effectiveness.

The present invention provides a group of new nitroimidazolyl-triazolo-pyridazines which possess a surprisingly high anti-microbial activity in vitro, not only against bacteria but also against Trichomonas, and also in vivo (systemic effectiveness).

The compounds of the present invention are new nitroimidazolyl-triazolo-pyridazines of the general formula:

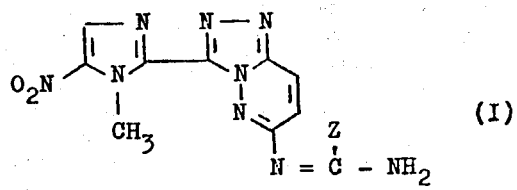

(I)

wherein
Z is methyl or amino which can be substituted by lower alkyl,
and the pharmacologically compatible acid-addition salts thereof.

The lower alkyl radical in the above-given general formula (I) preferably contains up to 3 carbon atoms.

The new compounds according to the present invention can be prepared, for example, by reacting a compound of the general formula:

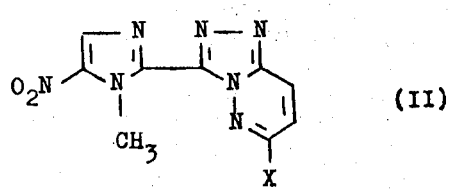

(II)

wherein
X is an amino group or a reactive residue, with a compound of the general formula:

(III)

wherein

Z has the same meaning as above, Y is a reactive residue or an amino group and A and B, which can be the same or different, represent lower alkoxy radicals or A and B together represent an imino group or A, B and Y, together with the carbon atom, represent a nitrile group, if necessary subsequently reacted with ammonia and the compound (I) thus obtained then, if desired, converted into a pharmacologically compatible acid-addition salt.

The reactive group X is preferably a halogen atom or a sulfonyl radical, such as methylsulfonyl or p-toluene-sulfonyl radicals and the reactive group Y is preferably a lower alkoxy or alkylthio radical.

The reaction of the compounds (II) and (III) can be carried out in an organic solvent, for example, in dimethyl sulfoxide, optionally in admixture with water, and with the addition of a base, the reaction preferably being carried out at an elevated temperature.

The possibly necessary subsequent reaction with ammonia is preferably carried out at ambient temperature in an organic solvent, for example, in dioxan or a lower alcohol, optionally in admixture with water.

The pharmacologically compatible salts can be prepared, for example, by neutralization of the free amino group of the compounds of general formula (I) with a non-toxic inorganic or organic acid. Examples of such acids include hydrochloric acid, sulfuric acid, phosphoric acid, hydrobromic acid, acetic acid, lactic acid, citric acid, oxalic acid, malic acid, salicylic acid, malonic acid, maleic acid, succinic acid and alkyl-sulfonic acids.

The following Examples are given for the purpose of illustrating, without limiting, the preparation of the compounds of the present invention:

EXAMPLE 1

3-(5-Nitro-1-methyl-2-imidazolyl)-6-(diaminomethyleneamino)-s-triazolo[4,3-b]pyridazine 3.36 g 3-(5-nitro-1-methyl-2-imidazolyl)-6-chloro-s-triazolo[4,3-b]pyridazine were dissolved in 30 ml. dimethyl sulfoxide and mixed at 70°C., while stirring, with 3.4 g guanidinium chloride. 5 ml. water were then added thereto, followed by the dropwise addition of 2.4 ml. 10N aqueous sodium hydroxide solution, whereafter the reaction mixture was further stirred for an hour at 70°C. After cooling and diluting with water, the precipitated crystals were filtered off with suction, washed with water and dried in a vacuum. 2.5 g of crude product were thus obtained which, after recrystallization from 25 ml. dimethyl formamide, with the addition of active charcoal, gave 1.17 g 3-(5-nitro-1-methyl-2-imidazolyl)-6-(diaminomethylene-amino)-s-triazolo [4,3-b] pyridazine in the form of a yellow material which melted, with decomposition, at 278° – 280°C.

EXAMPLE 2

3-(5-Nitro-1-methyl-2-imidazolyl)-6-(C-amino-, C-methylamino-methyleneamino)-s-triazolo[4,3-b]pyridazine 3.36 g 3-(5-nitro-1-methyl-2-imidazolyl)-6-chloro-s-triazolo[4,3-b]pyridazine were dissolved in 30 ml. dimethyl sulfoxide and mixed at 70°C., while stirring, with 4.9 g methyl-guanidinium nitrate, 2.4 ml. 10N aqueous sodium hydroxide were then slowly added dropwise and, 5 minutes afterwards, the reaction mixture was mixed with 6 ml. water and then stirred for an hour at 70°C. After cooling, the reaction mixture was diluted with water and the precipitated crystals were filtered off with suction, washed with water and dried in a vacuum. There was obtained 1.63 g of crude product which was recrystallized from 30 ml. of a mixture of dimethyl formamide and dioxan (3:2), with the addition of active charcoal. In this way, there was obtained 1.03 g 3-(5-nitro-1-methyl-2-imidazolyl)-6-(C-amino-, C-methylamino-methyleneamino)-s-triazolo[4,3-b] pyridazine in the form of a yellow product which melted, with foaming, at 271° – 273°C.

EXAMPLE 3

3-(5-Nitro-1-methyl-2-imidazolyl)-6-(C-amino-, C-ethylamino-methyleneamino)-s-triazolo[4,3-b]pyridazine In a manner analogous to that described in Example 2, from 3.92 g 3-(5-nitro-1-methyl-2-imidazolyl)-6-chloro-s-triazolo[4,3-b]pyridazine in 35 ml. dimethyl sulfoxide, 5.7 g ethyl-guanidinium sulfate, 2.8 ml. 10N aqueous sodium hydroxide solution and 7 ml. water, there were obtained, after a reaction time of 30 minutes at 70°C., 2.33 g 3-(5-nitro-1-methyl-2-imidazolyl)-6-(C-amino-, C-ethylamino-methyleneamino)-s-triazolo[4,3-b]pyridazine. After recrystallization from 40 ml. of a mixture of 80% dimethyl formamide and 20% dioxan, with the addition of active charcoal, this gave 1.63 g of pure product in the form of a yellow material which melted, with foaming, at 255° – 258°C.

EXAMPLE 4

N-[3-(5-Nitro-1-methyl-2-imidazolyl)-s-triazolo[4,3-b]pyridazin-6-yl]-acetamidine

VARIANT I 2 g 3-(5-Nitro-1-methyl-2-imidazolyl)-6-amino-s-triazolo [4,3-b]pyyridazine were stirred with 20 ml. ethyl orthoacetate and 10 ml. acetic anhydride for 30 minutes at 130°C. The reaction mixture was then evaporated in a vacuum at 70°C. and the residue was dissolved in 30 ml. of a mixture of isopropanol and dioxan (7:3), mixed with active charcoal, filtered and the clear filtrate mixed, while stirring at ambient temperature, with 3 ml. concentrated aqueous ammonia solution. After about 15 minutes, the precipitated crystals were filtered off with suction, washed with isopropanol and ether and dried in a vacuum at 110°C. There was obtained 1.88 g N-[3-(5-nitro-1-methyl-2-imidazolyl)-s-triazolo[4,3-b]pyridazin-6-yl]-acetamidine which melted, with foaming, at 256° – 260°C.

VARIANT II:

0.3 g 3-(5-Nitro-1-methyl-2-imidazolyl)-6-chloro-s-triazolo[4,3-b]pyridazine and 0.1 g acetamidinium chloride were dissolved in 30 ml. dimethyl sulfoxide and, after the addition of 0.3 ml. triethylamine, stirred at 150°C. After an hour, the reaction mixture was cooled and mixed with water. The precipitated crystals were filtered off with suction and then washed with water. The identity of the 0.15 g of crude product obtained after drying was found, by means of mass spectroscopy and chromatography, to be identical with the product obtained according to Variant I above. The product can be further purified by recrystallization from dimethyl formamide.

As noted above, the new nitroimidazolyl-triazolopyridazine compounds possess outstanding in vitro and in vivo antimicrobial action, against bacteria and Protozoa, such as Trichomonades and Salmonellae, which may be present in the digestive or other systems of mammals. This utility is, of course, shared by the pharmacologically acceptable salts of the pyridazine compounds, which salts are conventional in the art.

The antimicrobial activity of the instantly disclosed compounds was confirmed by the testing of a number of representative or illustrative compounds in certain tests. In one series of tests, the absolute bacteriostatic minimum concentration for each test compound was determined and expressed in micrograms per milliliter. Thus, Table 1 below sets forth, for each test compound, the maximum extent to which the test compound in question can be diluted and still exhibit bacteriostatic activity. As a comparison substance, there was used the commercial bacteriostat known as "Furadantin," which is identified chemically as N-(5-nitrofuryliden)-1-amino-hydantoine. It will be seen from the data presented in Table 1 that the instantly claimed compounds are substantially more active as bacteriostats than the comparison compound, i.e., Furadantin, in that much lower concentrations of the test compounds were capable of acting bacteriostatically, relative to the higher dosages of Furadantin required to achieve this effect. The data for Furadantin are presented at the end of Table 1 infra.

The following were the test compounds of the invention:

Compound I - N-[3-(5-nitro-1-methyl-2-imidazolyl)-s-triazolo[4,3-b]pyridazin-6-yl]-acetamidine Compound II - 3-(5-nitro-1-methyl-2-imidazolyl)-6-(diamino-methyleneamino)-s-triazolo[4,3-b]pyridazine Compound III - 3-(5-nitro-1-methyl-2-imidazolyl)-6-(C-amino-,C-methylamino-methyleneamino)-s-triazolo[4,3-b]pyridazine Compound IV - 3-(5-nitro-1-methyl-2-imidazolyl)-6-(C-amino,C-ethylamino-methyleneamino)-s-triazolo[4,3-b]pyridazine The results of the foregoing tests are set forth in Table 1 below.

TABLE 1

Bacteriostatic Effect In Vitro
Comparison Compound: Nitrofurantoin (Furadantin)

| Group Bacteria | Bacteria Type ( ) Strain | Absolute Bacteriostatic Minimum Concentration in μg/ml for: | | | | |
|---|---|---|---|---|---|---|
| | | Compound I | Compound II | Compound III | Compound IV | Furadantin |
| Gram-positive Bacteria | Staphylococcus aureus, SG 511 (12) | 8 | 8 | 8 | 16 | 16 |
| | Streptococcus pyogenes (92) | 1 | 1 | 0.5 | 1 | 8 |
| | Streptococcus faecalis (155) | 2 | 4 | 2 | 0.5 | 16 |
| Gram-negative Bacteria | Escherichia coli (108) | 0.125 | 0.062 | 0.031 | 0.008 | 4 |

TABLE 1-continued

Bacteriostatic Effect In Vitro
Comparison Compound: Nitrofurantoin (Furadantin)

| Group Bacteria | Bacteria Type ( ) Strain | Absolute Bacteriostatic Minimum Concentration in µg/ml for: | | | | |
|---|---|---|---|---|---|---|
| | | Compound I | Compound II | Compound III | Compound IV | Furadantin |
| | Escherichia coli (106) | 0.125 | 0.125 | 0.062 | 0.125 | 4 |
| | Proteus mirabilis (298) | 8 | 32 | 4 | >16 | 256 |
| | Klebsiella Pneumoniae (168) | 0.125 | 0.125 | 0.062 | 0.062 | 16 |
| | Pseudomonas aeruginosa (71) | 16 | 64 | >256 | >16 | >128 |

In another series of tests, the bacteriostatic activity of certain illustrative compounds of this invention in urine was tested and the percentage of administered test substance excreted in the urine was determined, after oral administration, in rats. Again, the comparison substance "Furadantin" (nitrofurantoin) was used in side-by-side comparisons. The results obtained are set forth in Table 2 below, in which the column headed "Maximal Dilution" represents the maximum extent to which a urine sample could be diluted and still exhibit bacteriostatic activity against the test bacterium, which was *Escherichia Coli* (106). The test compounds were administered at the rate 80 mg (or in the asterisked instances, 20 mg) of test compound per kg of the rat's body weight, and are on the basis of 75 ml of urine per 22 hours after oral administration of the test compound. Each test value is based on the averages of values obtained in tests in nine rats and in the instances where two values are set forth, two determinations were made. The corresponding value for the reference standard "Furadantin" are set forth at the bottom of Table 2. It can be seen that the compounds representative of the instant invention were capable of being diluted to a substantially greater extent than Furadantin, and still exhibit bacteriostatic activity; also, most of the compounds of the invention were excreted in urine to a much greater extent than Furadantin.

In yet an additional series of tests, the trichomonacidal activity of certain of the compounds of the invention in vitro was determined, against *Trichomonas vaginalis Carneri* species, expressed in the minimum concentration, in micrograms per milliliter, needed to exhibit trichomonacidal action. In these series of tests, the results of which are set forth in Table 3 below, the comparison substance was "Clont," which is chemically identified as 1-(2'-hydroxyethyl)-2-methyl-5-nitro-imidazole (=Flagyl). It can be seen from the data in Table 3 that three out of the four test compounds of the invention were active at much lower concentrations than Clont against the Trichomonas species, and that the fourth exhibited activity already at the low end dosage of the activity range of Clont.

TABLE 3

Trichomonacidal Effect In Vitro

| Substance | Trichomonacidal Minimum Concentration in µg/ml |
|---|---|
| *Clont | 0,5 – 1 |
| N-[3-(5-nitro-1-methyl-2-imidazolyl)-s-triazolo[4,3-b]pyridizin-6-yl]-acetamidine | 0.062 |
| 3-(5-nitro-1-methyl-2-imidazolyl)-6-(diamino-methyleneamino)-s-triazolo[4,3-b]pyridazine | 0.5 |
| 3-(5-nitro-1-methyl-2-imidazolyl)-6-(C-amino-,C-methylamino-methyleneamino)-s-triazolo[4,3-b]pyridazine | 0.062 |
| 3-(5-nitro-1-methyl-2-imidazolyl)-6-(C-amino,C-ethylamino-methyleneamino)-s-triazolo[4,3-b]pyridazine | 0.062 |

*Used as a comparison substance.

The compounds of general formula (I) and the salts thereof can be administered orally and parenterally in liquid or solid form. As injection medium, it is preferred to use water which contains the stabilizing agents, solubilizing agents and/or buffers conventional for injection solutions. Additives of this type include, for example, tartrate and borate buffers, ethanol, dimethyl sulfoxide, complex-forming agents (such as ethylenediamine-tetra-acetic acid), high molecular weight polymers (such as liquid polyethylene oxide) for viscosity regulation and polyoxyethylene derivatives of sorbitol anhydrides.

TABLE 2

Bacteriostatic Activity In Urine in Rats after Oral Administration

| Test Substance | Maximal Dilution |
|---|---|
| N-[3-(5-nitro-1-methyl-2-imidazolyl)-s-triazolo-[4,3-b]pyridazin-6-yl]-acetamidine | 1:660* |
| 3-(5-nitro-1-methyl-2-imidazolyl)-6-(diamino-methyleneamino-s-triazolo[4,3-b]pyridazine | 1:256 |
| | 1:347 |
| 3-(5-nitro-1-methyl-2-imidazolyl)-6-(C-amino-,C-methylamino-methyleneamino)-s-triazolo[4,3-b]pyridazine | 1:296* |
| | 1:447 |
| 3-(5-nitro-1-methyl-2-imidazolyl)-6-(C-amino,C-ethylamino-methyleneamino)-s-triazolo[4,3-b]pyridazine | 1:158* |
| Furadantin | 1:20 to 1:59* |

*In these tests 20 mg of test substance (rather than 80 mg) were employed.

Examples of solid carrier materials which can be used include starch, lactose, mannitol, methyl-cellulose, talc, highly dispersed silicic acid, high molecular fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening agents. For topical application, the new compounds (I) and the salts thereof can be used in the form of powders and salves; for this purpose, they are mixed with, for example, powdered, physiologically compatible diluents or with conventional salve bases.

The particular mode of administration and dosage of inventive compound to be applied in treating a given bacterial infection or infirmity will, of course, be determined by the physician, taking into account all the circumstances of a particular case. However, in general, tablets containing the test compound to be administered per os, will contain about 250 mg of active material and, for local administration, may contain about 500 mg of active substance. The dosage to be applied may be one tablet taken in the morning and in the evening with the corresponding meal, for, e.g., 10 consecutive days, if the compound is applied per os. For local administration, one ovule may be applied for 10 to 20 days every evening. In men, the per os administration may have to be increased to, e.g., 750 mg to 1 g, instead of the standard 250 mg per tablet dosage.

The compounds of this invention can thus be described as anti-parasiticides with specific activity against *Trichomonas vaginalis*, as well as *Lamblia intestinales* and *Entamoeba histolitica*, and the materials of the invention are active not only locally, but per os.

In general, the compounds of the invention exhibit similar activity, but, in most instances, to a greater degree, as the commercial material known as Flagyl, marketed by Etablissements R. Barberot S.A., Geneva, Switzerland.

It will be understood that the specification and examples are illustrative but not limitative of the present invention and that other embodiments within the spirit and scope of the invention will suggest themselves to those skilled in the art.

What is claimed is:

1. Nitroimidazolyl-triazolo-pyridazine compound of the formula:

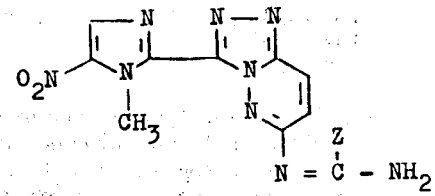

wherein
Z is amino, or monolowerakylamino, and the pharmacologically compatible acid-addition salts thereof.

2. Nitroimidazolyl-triazolo-pyridazine compound as claimed in claim 1 wherein Z is amino.

3. Nitroimidazolyl-triazolo-pyridazine compound as claimed in claim 1 wherein Z is alkylamino of up to 3 carbon atoms.

4. Nitroimidazolyl-triazolo-pyridazine compound as claimed in claim 1 designated 3-(5-nitro-1-methyl-2-imidazolyl) 6-(diamino-methyleneamino)-s-triazolo[4,3-b]pyridazine.

5. Nitroimidazolyl-triazolo-pyridazine compound as claimed in claim 1 designated 3-(5-nitro-1-methyl-2-imidazolyl)-6-(C-amino-, C-methylamino-methyleneamino)-s-triazolo[4,3-b]-pyridazine.

6. Nitroimidazolyl-triazolo-pyridazine compound as claimed in claim 1 designated 3-(5-nitro-1-methyl-2-imidazolyl)-6-(C-amino-, C-ethylamino-methyleneamino)-s-triazolo[4,3-b]-pyridazine.

* * * * *